(12) United States Patent
Kim et al.

(10) Patent No.: US 10,016,622 B2
(45) Date of Patent: Jul. 10, 2018

(54) DOSE CALCULATION METHOD, DOSE CALCULATION DEVICE, AND COMPUTER-READABLE STORAGE MEDIUM

(71) Applicant: IUCF-HYU (INDUSTRY-UNIVERSITY COOPERATION FOUNDATION HANYANG UNIVERSITY), Seoul (KR)

(72) Inventors: Chan Hyeong Kim, Seoul (KR); Seong Hoon Kim, Seoul (KR); Min Cheol Han, Seoul (KR); Yeon Soo Yeom, Chungcheongbuk-do (KR); Se Hyung Lee, Seoul (KR)

(73) Assignee: ICUF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 0 days.

(21) Appl. No.: 15/128,551

(22) PCT Filed: May 19, 2014

(86) PCT No.: PCT/KR2014/004470
§ 371 (c)(1),
(2) Date: Sep. 23, 2016

(87) PCT Pub. No.: WO2015/147372
PCT Pub. Date: Oct. 1, 2015

(65) Prior Publication Data
US 2017/0128745 A1 May 11, 2017

(30) Foreign Application Priority Data

Mar. 26, 2014 (KR) ........................ 10-2014-0035591

(51) Int. Cl.
*G06K 9/00* (2006.01)
*A61N 5/10* (2006.01)
(Continued)

(52) U.S. Cl.
CPC .......... *A61N 5/1031* (2013.01); *A61N 5/1037* (2013.01); *A61N 5/1039* (2013.01);
(Continued)

(58) Field of Classification Search
CPC .................................. A61N 5/00; G06T 7/00
(Continued)

(56) References Cited

U.S. PATENT DOCUMENTS 5,341,292 A * 8/1994 Zamenhof ............ A61N 5/1031
600/410
8,597,211 B2 * 12/2013 Berlinger .............. G06T 7/0044
340/573.1

(Continued)

OTHER PUBLICATIONS

The extended European Search Report dated Nov. 7, 2017; Appln. 14887216.1.

*Primary Examiner* — Abolfazl Tabatabai
(74) *Attorney, Agent, or Firm* — Ladas & Parry LLP

(57) ABSTRACT

Provided are a dose calculation method, a dose calculation device, and a computer-readable storage medium. The dose calculation method comprises: generating an intermediate image between a plurality of sequentially acquired diagnostic images; and calculating doses through a simulation using the diagnostic images and the intermediate image.

12 Claims, 10 Drawing Sheets

(51) Int. Cl.
  *G06T 7/00* (2017.01)
  *G16H 50/50* (2018.01)
  *H05G 1/42* (2006.01)
  *A61M 5/00* (2006.01)

(52) U.S. Cl.
  CPC ........... *G06T 7/0016* (2013.01); *G16H 50/50* (2018.01); *A61N 2005/1034* (2013.01); *A61N 2005/1035* (2013.01); *G06T 2207/10016* (2013.01); *G06T 2207/10081* (2013.01); *G06T 2207/30061* (2013.01)

(58) Field of Classification Search
  USPC ............. 382/128–134; 378/97, 108; 600/246
  See application file for complete search history.

(56) References Cited

U.S. PATENT DOCUMENTS

| | | | |
|---|---|---|---|
| 9,528,979 B2 * | 12/2016 | Haick | .................. G01N 33/497 |
| 2003/0169254 A1 | 9/2003 | Ditt et al. | |
| 2008/0081991 A1 | 4/2008 | West et al. | |

\* cited by examiner

N DIAGNOSTIC IMAGES

FIG. 4
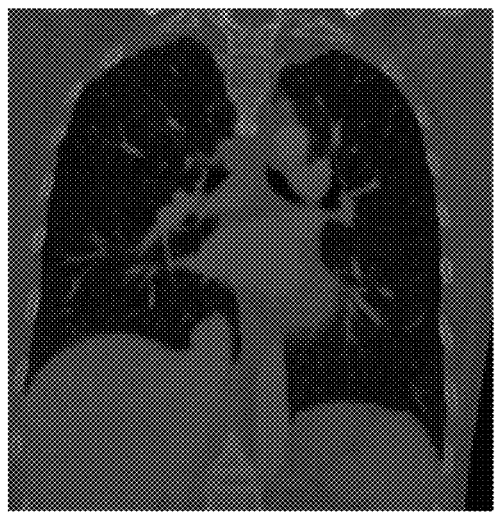
(A) RTH DIAGNOSTIC IMAGE
(C) ACQUIRE DEFORMABLE VECTOR FIELD
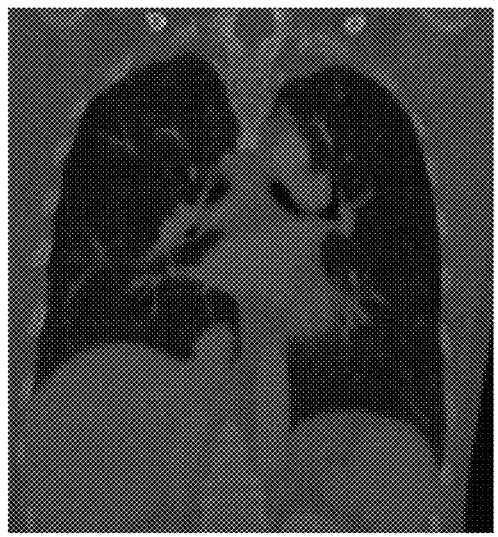
(B) R+1TH DIAGNOSTIC IMAGE

DOSE CALCULATION METHOD, DOSE CALCULATION DEVICE, AND COMPUTER-READABLE STORAGE MEDIUM

CROSS REFERENCE TO RELATED APPLICATIONS

This application is a National Stage of International Application No. PCT/KR2014/004470, filed May 19, 2014, and claims priority Korean Patent Application No. 10-2014-0035591 flied Mar. 26, 2014, the contents of which are incorporated herein by reference in their entireties.

TECHNICAL FIELD

The inventive concept relates to a dose calculation method, a dose calculation device, and a computer-readable storage medium, and more particularly, to a dose calculation method, a dose calculation device, and a computer-readable storage medium calculating doses by using sequentially acquired four-dimensional (4D) computed tomography (CT) images.

BACKGROUND ART

In order to increase an effect of cancer treatment without damage of normal tissue by irradiating cancer tissue with an optimal radiation dose for cancer tissue and irradiating normal tissue around the cancer tissue with a minimum radiation dose at the same time during radiation treatment for cancer, research on radiation treatment planning (RTP) to make a plan for a radiation dose according to a state of cancer in a patient has been performed.

The RTP, which is related to calculation and verification of a radiation dose and generation of radiation treatment information, is made through a computer simulation using diagnostic images of a patient, for example, 3D computed tomography (CT) images or average intensity projection (AVE-IP) of 4D CT images.

The diagnostic images of the patient cannot reflect movement of internal organs according to breathing, and thus, may cause a difference between a dose of RTP and a dose of actual radiation treatment. A greater dose difference may occur especially when RTP about a tumor generated in an organ with a large movement, for example, a lung, a liver, or a pancreas. Furthermore, a much greater dose difference may occur when radiation treatment using charged particles irradiating a local area with many doses or spot-scanning radiation treatment irradiating a tumor of a patient with radiation by moving a beam along a shape of the tumor is performed. However, if a breathing period of a patient is further subdivided to reflect movement of the internal organ to prevent the dose difference, and thus, more diagnostic images are acquired and an exposure dose of the patient may increase.

In general, a calculation of a dose when making RTP includes a separate process of calculating a dose of each of diagnostic images of a patient by performing a computer simulation and matching each of the dose calculation results with a specific reference image. As a result, a time for RTP is longer and it is difficult to simplify and automate a dose calculation process.

DETAILED DESCRIPTION OF THE INVENTION

Technical Problem

The inventive concept provides a dose calculation method, a dose calculation device, and a computer-readable storage medium capable of reducing a dose difference according to movement of an internal organ of a patient without acquiring additional 4D computed tomography (CT) images, and capable of reducing a dose calculation time and simplifying a dose calculation process.

Technical Solution

According to an aspect of the inventive concept, there is provided a dose calculation method comprising: generating an intermediate image between a plurality of diagnostic images that are sequentially acquired; and calculating a dose through a simulation using the diagnostic images and the intermediate image.

According to an exemplary embodiment, wherein the generating the intermediate image may comprise: acquiring a deformable vector field indicating a moving direction of voxels between the diagnostic images; and generating the intermediate image based on the deformable vector field and a function representing breathing of a patient.

According to an exemplary embodiment, wherein the function representing the breathing of the patient may be acquired by measuring breathing characteristics of the patient.

According to an exemplary embodiment, wherein the calculating the dose may comprise: calculating a dose of each of the intermediate image and the diagnostic images; and recalculating the calculated dose of each of the intermediate image and the diagnostic images to correspond to a reference image by referring to the deformable vector field.

According to an exemplary embodiment, wherein the diagnostic images may be 4D computed tomography (CT) images, and the computer simulation may be a deterministic simulation or a stochastic simulation.

According to another aspect of the inventive concept, there is provided a dose calculation device comprising: an intermediate image generation unit configured to generate an intermediate image between a plurality of diagnostic images that are sequentially acquired; and a dose calculation unit configured to calculate a dose through a simulation using the plurality of diagnostic images and the intermediate image.

According to an exemplary embodiment, wherein the intermediate image generation unit may comprise a deformable vector field acquisition unit acquiring a deformable vector field indicating a moving direction of voxels between the diagnostic images, and may generate the intermediate image based on the deformable vector field.

According to an exemplary embodiment, the dose calculation device may further comprise: a storage unit configured to store a function representing breathing of a patient, wherein the intermediate image generation unit generates the intermediate image based on the function and the deformable vector field.

According to an exemplary embodiment, wherein the function representing the breathing of the patient may be acquired by measuring breathing characteristics of a patient.

According to an exemplary embodiment, wherein the dose calculation unit may calculate a dose of each of the intermediate image and the diagnostic images, and recalculate the calculated dose of each of the intermediate image and the diagnostic images to correspond to a reference image by referring to the deformable vector field.

According to still another aspect of the inventive concept, there is provided a non-transitory computer-readable storage medium having saved thereon at least one program comprising commands for executing the aforementioned dose calculation method by a processor of a computer when the program is executed by the computer.

Advantageous Effects

According to a dose calculation method and a dose calculation device according to the inventive concept, a dose difference may be reduced without increase in an exposure of a patient by generating intermediate images between continuous 4D computed tomography (CT) images to reflect movement of an internal organ of a patient without acquiring additional images and calculating a dose, and thus, it is possible to make accurate radiation treatment planning (RTP) and radiation treatment.

Furthermore, according to a dose calculation method and a dose calculation device according to the inventive concept, doses of 4D CT images and intermediate images sequentially acquired may be calculated and each of the calculated doses of the images may be recalculated with respect to a reference image through a single computer simulation, and thus, RTP may be rapidly made by reducing the total dose calculation time and simplification and automation of a dose calculation process may be possible.

DESCRIPTION OF THE DRAWINGS

Embodiments of the inventive concept will be more clearly understood from the following detailed description taken in conjunction with the accompanying drawings in which:

FIGS. 3 through 8 are views for describing operations of the dose calculation method of FIG. 2 in detail.

MODE OF THE INVENTION

Figure 1:
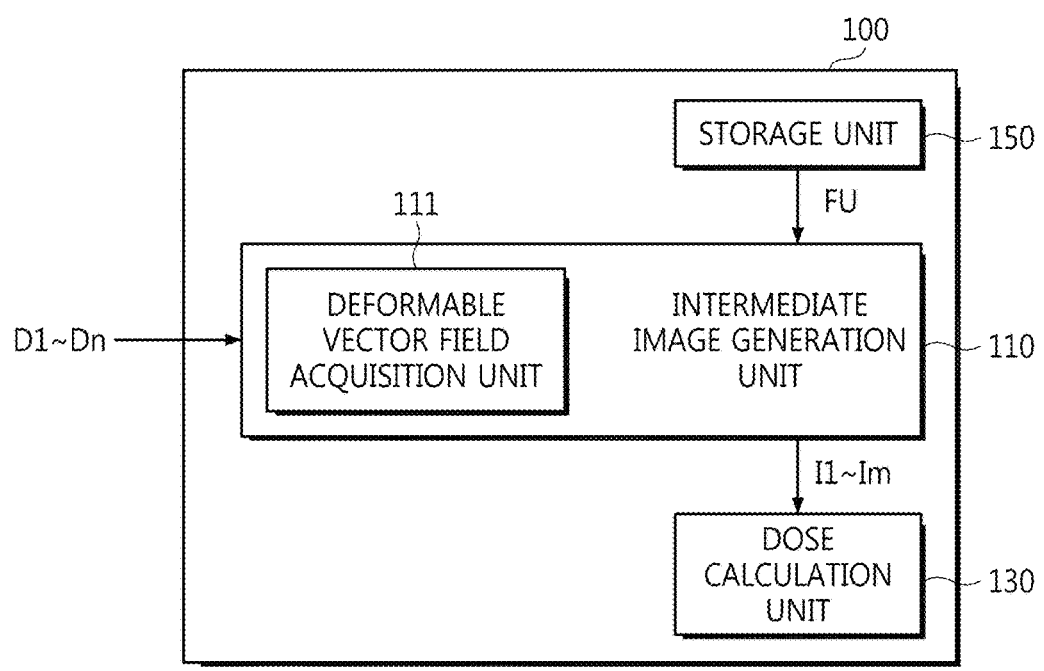
FIG. 1 is a schematic block diagram of a dose calculation device according to an embodiment of the inventive concept.

Since the inventive concept may have diverse modified embodiments, preferred embodiments are illustrated in the drawings and are described in the detailed description. However, this does not limit the inventive concept within specific embodiments and it should be understood that the inventive concept covers all the modifications, equivalents, and replacements within the idea and technical scope of the inventive concept.

In the description of the present disclosure, certain detailed explanations of the related art are omitted when it is deemed that they may unnecessarily obscure the essence of the inventive concept. While the terms including an ordinal number, such as "first", "second", etc., may be used to describe various components, such components are not be limited by these terms. The terms first and second should not be used to attach any order of importance but are used to distinguish one element from another element.

Throughout the specification, it will be understood that when a unit is referred to as being "connected" to another element, it may be "directly connected" to the other element or "electrically connected" to the other element in a state in which intervening elements are present.

In addition, terms such as " . . . unit", " . . . module", or the like refer to units that perform at least one function or operation, and the units may be implemented as hardware or software or as a combination of hardware and software.

Furthermore, components of the specification are divided in accordance with a main function of each component. For example, combining two or more elements are in a single component, as needed, or may be one component configuration is subdivided into two or more components. Each of the components may further perform some or all of the functions of other components as well as its main functions, and some of the main functions may also be performed by other components.

Hereinafter, embodiments of the inventive concept will be described in detail with reference to the accompanying drawings.

FIG. 1 is a schematic block diagram of a dose calculation device 100 according to an embodiment of the inventive concept. The dose calculation device 100 may be, by itself, a device for making radiation treatment planning (RTP), a device for verifying RTP, or a simulation treatment device, or may be a part of the device for making RTP, the device for verifying RTP, or the simulation treatment device.

Referring to FIG. 1, the dose calculation device 100 may include an intermediate image generation unit 110, a dose calculation unit 130, and a storage unit 150. FIG. 1 illustrates that the intermediate image generation unit 110, the dose calculation unit 130, and the storage unit 150 are separately included in the dose calculation device 100. However, the inventive concept is not limited thereto. At least two of the intermediate image generation unit 110, the dose calculation unit 130, and the storage unit 150 may be formed as a single structure.

The intermediate image generation unit 110 may receive n (n is a natural number of 2 or more) diagnostic images D1 through Dn that are sequentially acquired. The n diagnostic images D1 through Dn may be images that are acquired by a imaging device, for example, a 4D computed tomography (CT) device sequentially imaging an affected part (for example, an internal organ) of a patient at a predetermined time interval. In some embodiments, the n diagnostic images D1 through Dn may be images that are acquired by the imaging device imaging an affected part of a patient by dividing a breathing period of the patient into ten phases. The n diagnostic images D1 through Dn may be provided from the imaging device to the intermediate image generation unit 110.

The intermediate image generation unit 110 may include a deformable vector field acquisition unit 111 acquiring a deformable vector field by using the n diagnostic images D1 through Dn. For example, the deformable vector field acquisition unit 111 may calculate a moving direction of voxels between continuous two diagnostic images from among the n diagnostic images D1 through Dn such as a first diagnostic image D1 and a second diagnostic image D2. The deformable vector field acquisition unit 111 may calculate the moving direction of the voxels by using deformable image registration (DIR) for estimating movement between the two images by matching coordinate systems of the two images with each other. The DIR may use any one of, e.g., an optical flow algorithm, a level set algorithm, a demons algorithm, a b-spline algorithm, a free-style deformation algorithm, and an iterative sum-of-squared-difference (SSD) minimization algorithm. The deformable vector field acquisition unit 111 may acquire the deformable vector field indicating a directional group of each vector based on the calculated moving direction of the voxels. FIG. 1 shows that the deformable vector field acquisition unit 111 is included in the intermediate image generation unit 110, but is not limited thereto. The deformable vector field acquisition unit 111 may also be included in the calculation device 100 as distinct from the intermediate image generation unit 110.

The intermediate image generation unit 110, based on the deformable vector field acquired by the deformable vector field acquisition unit 111 and a function FU representing breathing of a patient, may generate an intermediate image between continuous two diagnostic images from among the sequentially acquired n diagnostic images D1 through Dn. For example, the intermediate image generation unit 110 may generate an intermediate image corresponding to a gap between the first and second diagnostic images D1 and D2 through interpolation using the deformable vector field acquired by using the first and second diagnostic images D1 and D2 and the function FU. The function FU may be provided from the storage unit 150. A plurality of intermediate images may be generated one by one between each of continuous two diagnostic images. However, the inventive concept is not limited thereto, and each intermediate image between continuous two diagnostic images may be at least two. Hereinafter, for convenience of description, it will be described that m (m is a natural number) intermediate images I1 through Im in total are generated as intermediate images are generated one by one between continuous two diagnostic images.

The dose calculation unit 130 may receive the n diagnostic images D1 through Dn. As illustrated in FIG. 1, the dose calculation unit 130 receives the n diagnostic images D1 through Dn through the intermediate image generation unit 110, however, the dose calculation unit 130 is not limited thereto. The dose calculation unit 130 may directly receive the n diagnostic images D1 through Dn from the imaging device (not shown).

The dose calculation unit 130 may receive the m intermediate images I1 through Im from the intermediate image generation unit 110. Furthermore, the dose calculation unit 130 may receive the deformable vector field from the intermediate image generation unit 110.

The dose calculation unit 130 may calculate a dose through a simulation of the n diagnostic images D1 through Dn and the m intermediate images I1 through Im. In detail, the dose calculation unit 130 may calculate a dose of each of the n diagnostic images D1 through Dn and the m intermediate images I1 through Im based on a position of an affected part of a patient in each of the n diagnostic images D1 through Dn and the m intermediate images I1 through Im. Next, the dose calculation unit 130 may recalculate the calculated dose of each of the n diagnostic images D1 through Dn and the m intermediate images I1 through Im to correspond to a reference image. In other words, the dose calculation unit 130 may estimate a converted position of the affected part of the patient corresponding to the reference image from any one of the n diagnostic images D1 through Dn and the m intermediate images I1 through Im by referring to the deformable vector field, and may further recalculate a dose calculated based on the estimated converted position of the affected part to correspond to the reference image. The reference image may be any one of the n diagnostic images D1 through Dn and/or the m intermediate images I1 through Im.

The dose calculation unit 130 may calculate a dose of each of the n diagnostic images D1 through Dn and the m intermediate images I1 through Im through, e.g., a deterministic simulation or a stochastic simulation. The deterministic simulation, which is a simulation using superposition/convolution, may be a simulation excluding probability application. The stochastic simulation may use probability. The stochastic simulation may be, for example, a Monte Carlo simulation. The Monte Carlo simulation may use, for example, a code for a GEometry ANd Tracking (GEANT4) code, a Monte Carlo N-particle (MCNP) code, an Electron-Gamma Shower (EGS) code, a FLUKA code, or a Particle and Heavy Ion Transport code System (PHITS) code.

The storage unit 150 may store the function FU representing breathing of a patient. The function FU representing breathing of a patient may indicate movement of an affected part (for example, an internal organ) of a patient according to the breathing of the patient. The function FU representing breathing of a patient may be acquired by directly measuring breathing characteristics of a patient. Alternatively, the function FU representing breathing of a patient may be selected from previously stored functions corresponding to breathing characteristics of a patient.

The storage unit 150 may provide the function FU representing breathing of a patient to the intermediate image generation unit 110, and accordingly, the intermediate image generation unit 110 may generate an intermediate image reflecting movement of an internal organ of a patient.

As such, the dose calculation device 100 may reduce a difference between a calculated dose and a dose of actual radiation treatment by generating the m intermediate images I1 through Im reflecting the movement of the internal organ of the patient in gaps between the n diagnostic images D1 through Dn without acquiring additional diagnostic images or more diagnostic images, and by using the m intermediate images I1 through Im generated during dose calculation with the n diagnostic images D1 through Dn. Therefore, the dose calculation device 100 may improve reliability during dose calculation in RTP, and may maximize an effect of radiation treatment by improving accuracy of radiation treatment.

Furthermore, the dose calculation device 100 may simplify and automate a dose calculation process by calculating doses of images corresponding to a reference image through a single simulation, and may rapidly make RTP by reducing a dose calculation time.

Figure 2:
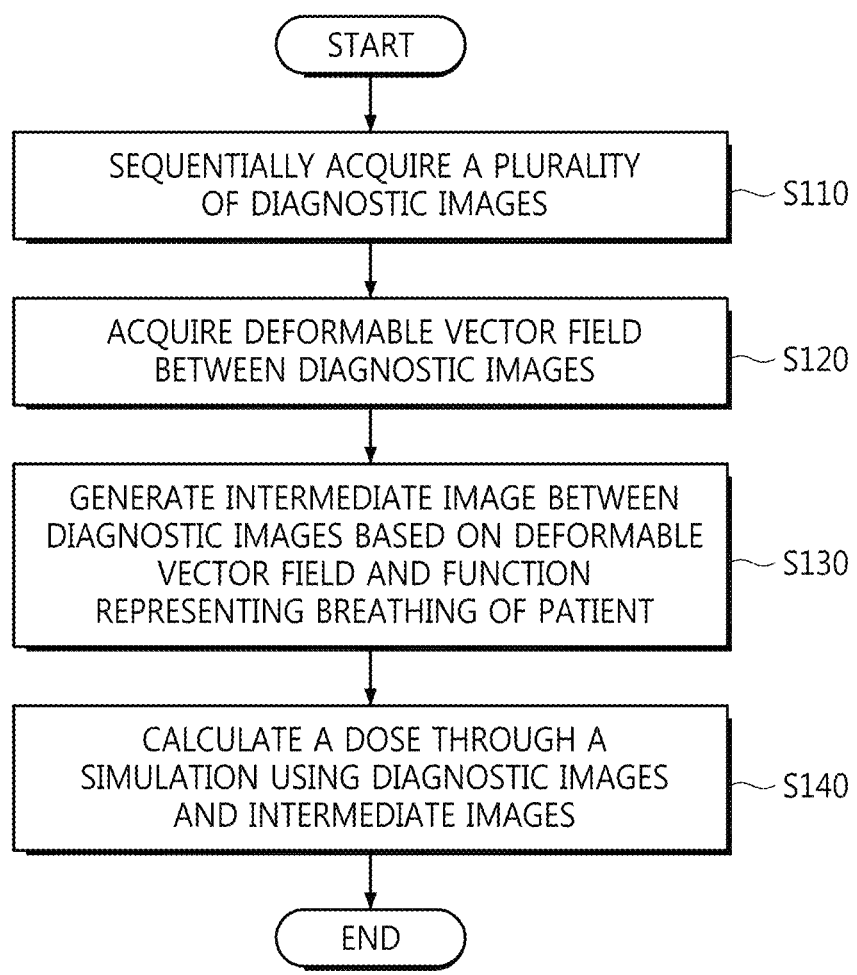
FIG. 2 is a flowchart for describing a dose calculation method according to an embodiment of the inventive concept.

FIG. 2 is a flowchart for describing a dose calculation method according to an embodiment of the inventive concept, and FIGS. 3 through 8 are views for describing operations of the dose calculation method of FIG. 2 in detail. Hereinafter, the dose calculation method according to an embodiment of the inventive concept will be described referring to FIGS. 2 through 8 as well as FIG. 1. The dose calculation method according to FIG. 2 may be implemented as a program and recorded on a non-transitory computer-readable recording medium, and the program may be installed in or downloaded to the dose calculation device 100 as described in FIG. 1, and thus, corresponding functions may be executed by a processor of the dose calculation device 100.

Figure 3:
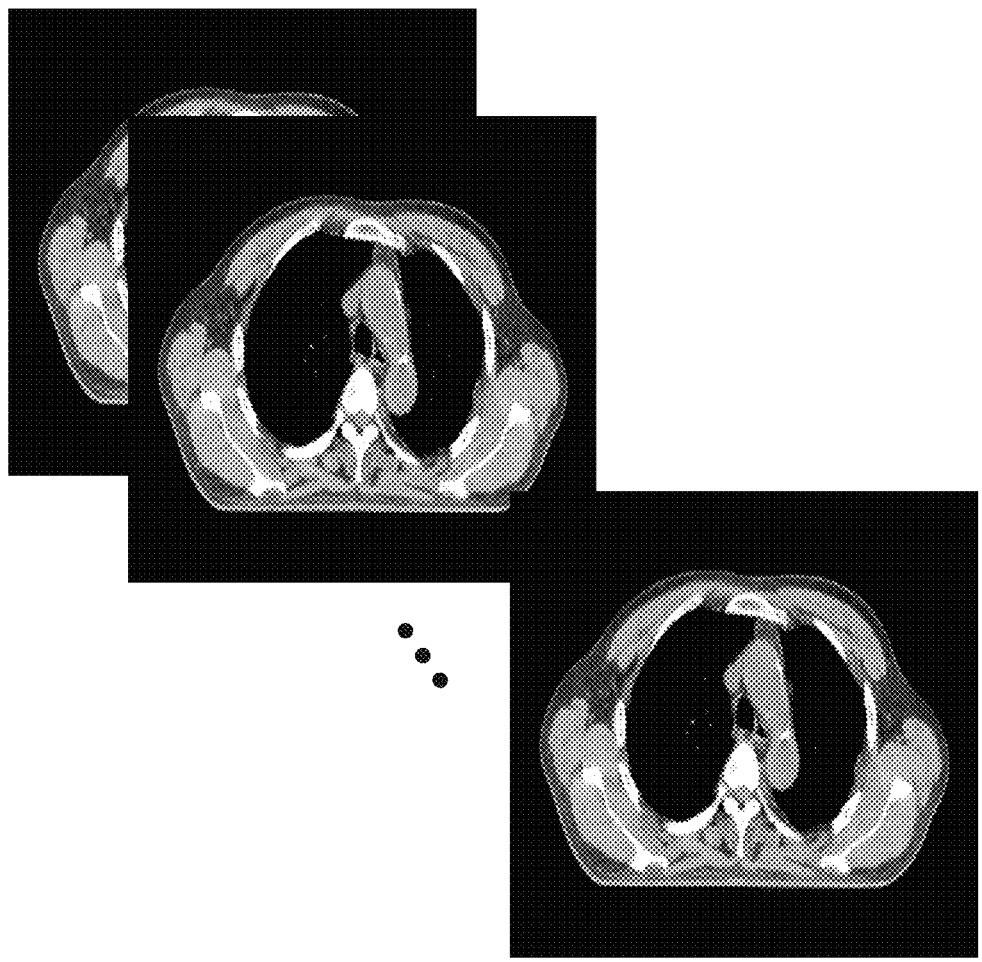

Referring to FIGS. 1 to 3, in operation S110, a plurality of diagnostic images are sequentially acquired by a imaging device (not shown). The imaging device may be a 4D CT device, and the diagnostic images may be a 4D CT images. The plurality of diagnostic images, which are acquired by imaging an affected part (for example, an internal organ) of a patient, may include n (n is a natural number of 2 or more) diagnostic images that are acquired by sequentially imaging the affected part of the patient at a predetermined time interval.

Referring to FIGS. 1 and 2, and 4, in operation S120, acquired is a deformable vector field between the n diagnostic images sequentially acquired by the dose calculation device 100. For example, the dose calculation device 100 may calculate a moving direction of voxels between continuous rth (r is a natural number less than n) diagnostic image and r+1th diagnosis image from among the n diagnostic images by using DIR, and may acquire the deformable vector field denoting a directional group of each vector. Similarly, the dose calculation device 100 may acquire a deformable vector field between other continuous diagnostic images from among the n diagnostic images.

Figure 5:
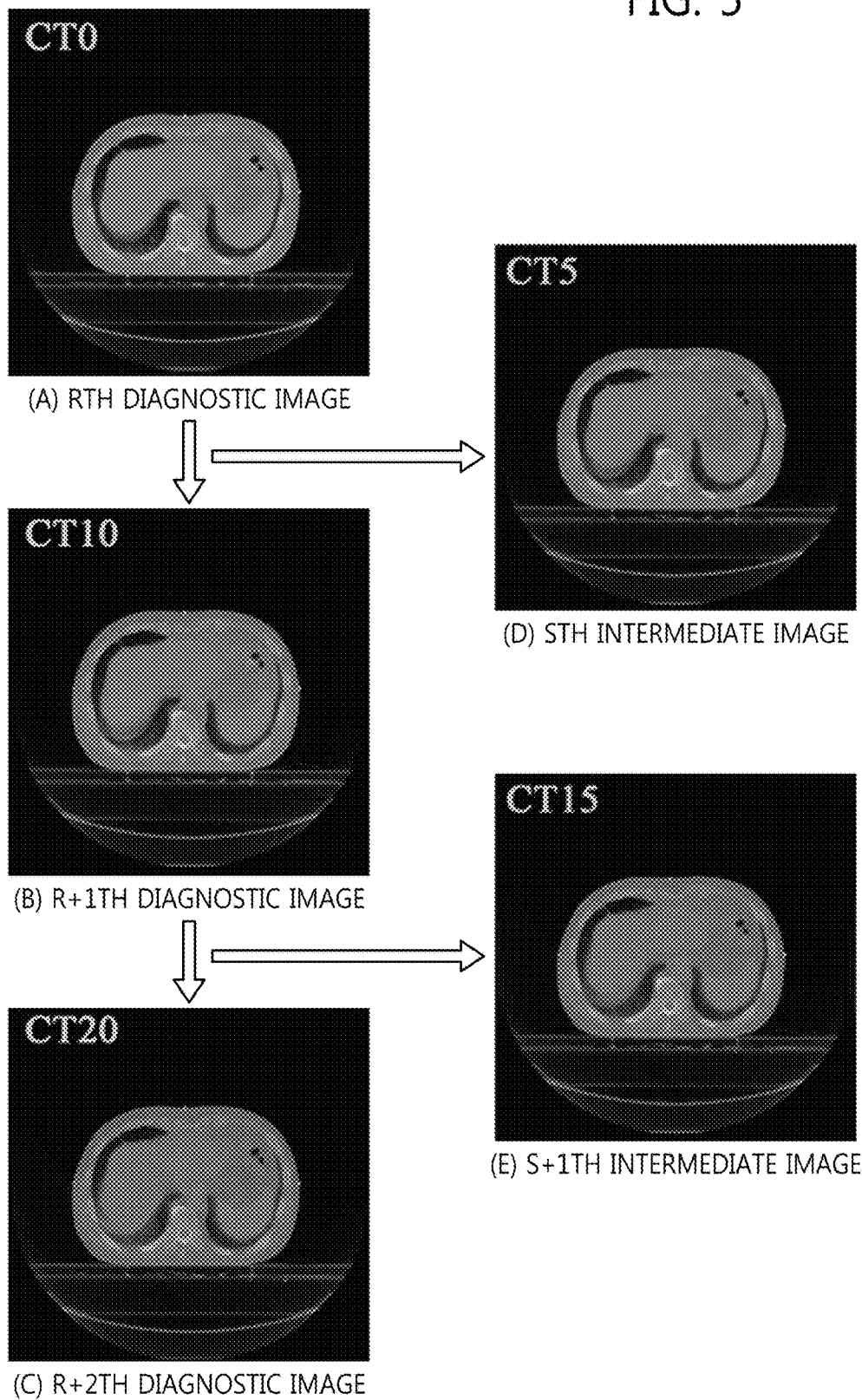
Figure 6:
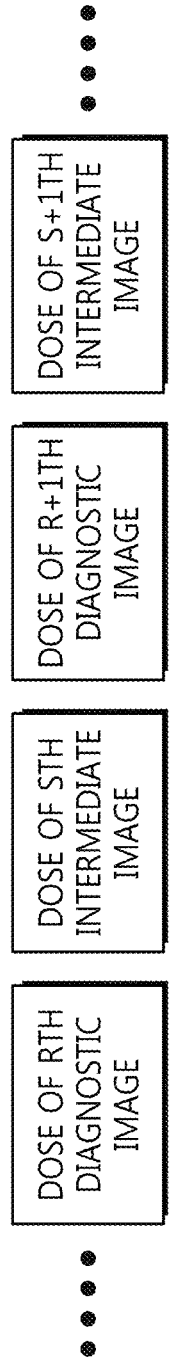
Figure 7:
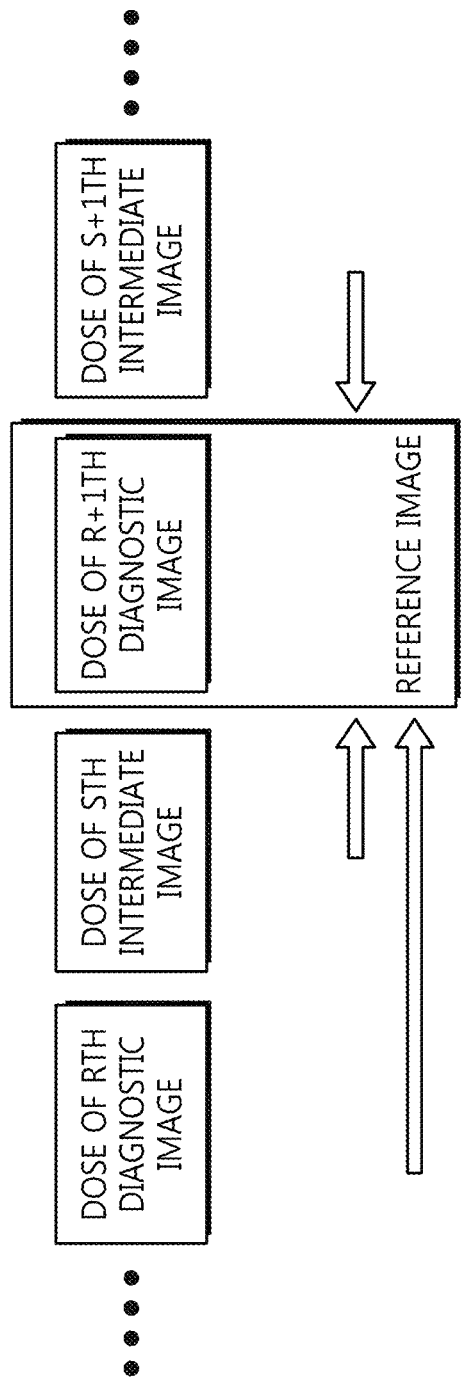

Referring to FIGS. 1 and 2, and 5, in operation S130, an intermediate image between diagnostic images is generated based on the deformable vector field acquired by the dose calculation device 100 and the function FU representing breathing of a patient. For example, the dose calculation device 100 may generate an sth (s is a natural number less than m) intermediate image between an rth diagnostic image and an r+1th diagnostic image through interpolation using the acquired deformable vector field and the function FU representing the breathing of the patient. Similarly, the dose calculation device 100 may generate an s+1th intermediate image between an r+1th diagnostic image and an r+2th diagnostic image based on a corresponding deformable vector field and the function FU representing the breathing of the patient. The dose calculation device 100 may generate m (m is a natural number) intermediate images in total by repeating operation S130. The function FU, which is acquired by measuring breathing characteristics of a patient, may indicate movement of an affected part of a patient according to the breathing of the patient.

Referring to FIGS. 1 and 2, and FIGS. 6 to 8, in operation S140, a dose is calculated by the dose calculation device 100 through a simulation using the n diagnostic images and the m intermediate images. For example, the dose calculation device 100 may calculate a dose of an affected part of a patient from each of the n diagnostic images including the rth and r+1th diagnostic images and the m intermediate images including the sth and s+1th intermediate images. Next, when the reference image is the r+1th diagnostic image, the dose calculation device 100 may refer to a deformable vector field between the rth diagnostic image and the r+1th diagnostic image and recalculate the calculated doses of the rth diagnostic image and the sth intermediate image to correspond to the r+1th diagnostic image. The dose calculation device 100 may recalculate the calculated doses of other images to correspond to the r+1th diagnostic image that is the reference image.

Figure 8:
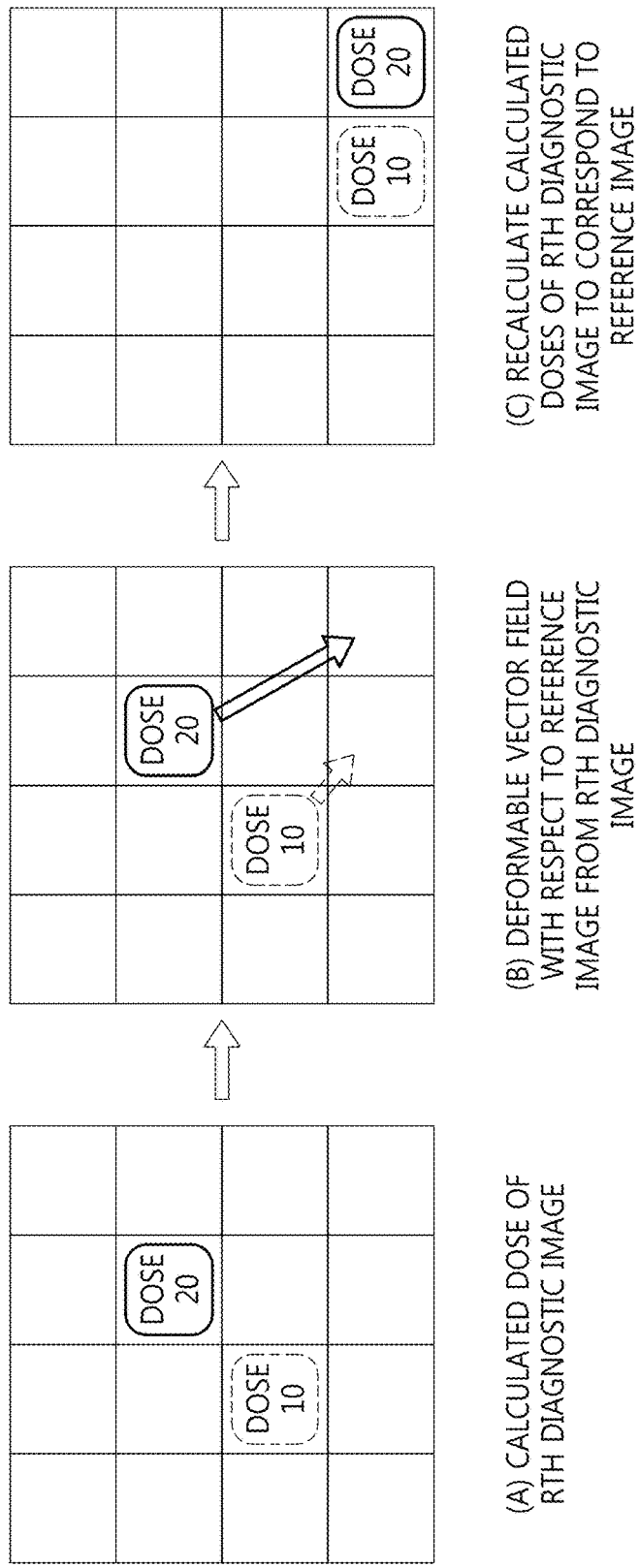

Further referring to FIG. 8 illustrating a dose calculation process with respect to the rth diagnostic image in detail, in operation S140, the dose calculation device 100 may calculate a dose based on a position of an affected part of a patient in the rth diagnostic image (FIG. 8(a)), may estimate a converted position of the affected part of the patient in the rth diagnostic image corresponding to the reference image by referring to a deformable vector field with respect to the reference image (r+1th diagnostic image) from the rth diagnostic image (FIG. 8(b)), and may recalculate the calculated dose of the rth diagnostic image based on the estimated converted position of the affected part (see FIG. 8(c)).

As such, the dose calculation method may improve reliability during dose calculation in RTP by reducing a dose difference, and may maximize an effect of radiation treatment by improving accuracy of radiation treatment. Furthermore, the dose calculation method may calculate doses of images corresponding to the reference image through one simulation, and thus, may rapidly make RTP by reducing a dose calculation time.

Figure 9:
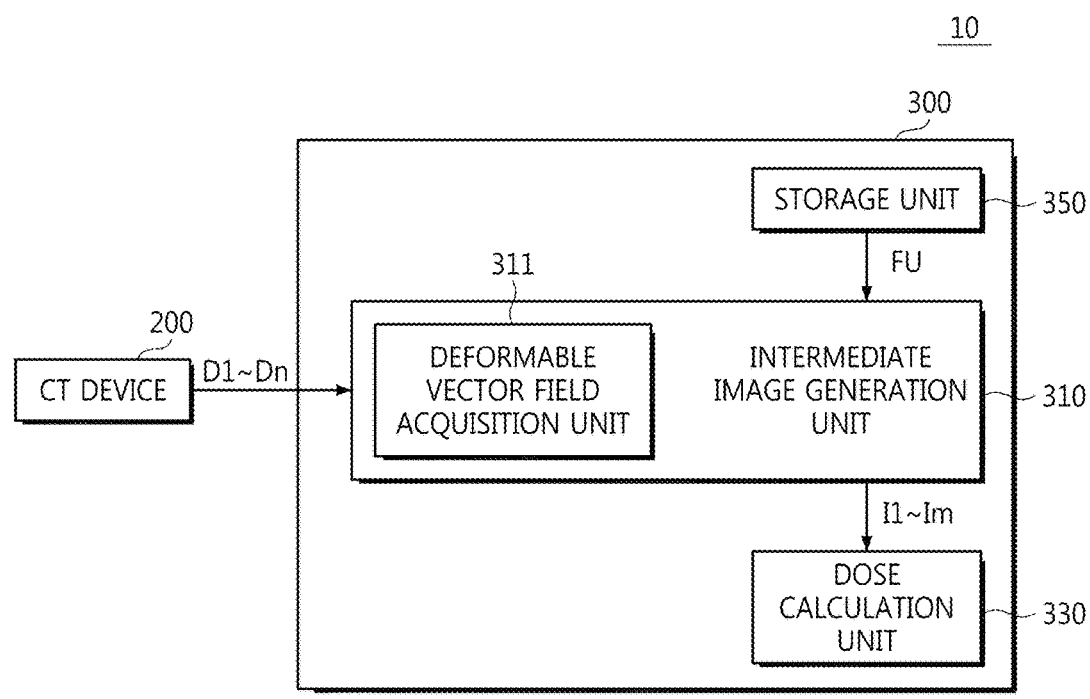
FIG. 9 is a schematic block diagram of a medical system according to an embodiment of the inventive concept.

FIG. 9 is a schematic block diagram of a medical system 10 according to an embodiment of the inventive concept. Referring to FIG. 9, the medical system 10 may include a imaging device 200 and a dose calculation device 300. The imaging device 200 may be, for example, a 4D CT device, and the dose calculation device 300 may correspond to the dose calculation device 100 of FIG. 1.

FIG. 9 illustrates that the dose calculation device 300 is independent from the imaging device 200. However, the inventive concept is not limited thereto. The dose calculation device 300 may be included in the imaging device 200.

The medical system 10 may rapidly and simply make RTP having improved reliability by reducing a dose difference.

Figure 10:
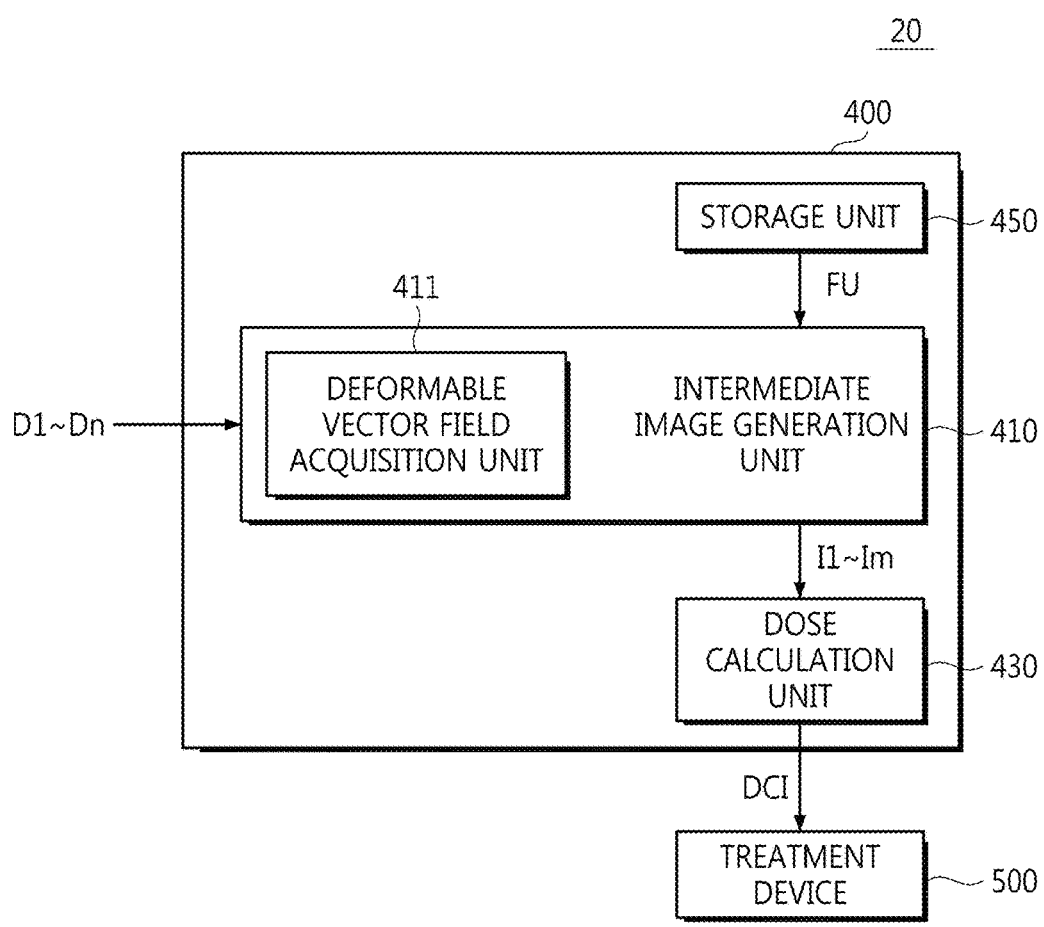
FIG. 10 is a schematic block diagram of a medical system according to another embodiment of the inventive concept.

FIG. 10 is a schematic block diagram of a medical system 20 according to another embodiment of the inventive concept. Referring to FIG. 10, the medical system 20 may include a dose calculation device 400 and a treatment device 500. The dose calculation device 400 may correspond to the dose calculation device 100 of FIG. 1, and the treatment device 500 may perform radiation treatment on a patient based on dose calculation information (DCI) provided from the dose calculation device 400. The DCI may be information generated based on a dose calculated by the dose calculation device 400.

FIG. 10 illustrates that the dose calculation device 400 is independent from the treatment device 500. However, the inventive concept is not limited thereto. The dose calculation device 400 may be included in the treatment device 500.

The medical system 20 may perform radiation treatment, by which the effect is maximized, based on DCI having improved reliability.

While the embodiments have been particularly shown and described, it will be understood by those of ordinary skill in the art that various changes in form and details may be made therein without departing from the spirit and scope of the inventive concept as defined by the appended claims.

The invention claimed is:

1. A dose calculation method comprising:
generating an intermediate image between a plurality of diagnostic images that are sequentially acquired; and
calculating a dose through a simulation using the diagnostic images and the intermediate image,
wherein the generating the intermediate image comprises:
acquiring a deformable vector field indicating a moving direction of voxels between the diagnostic images; and
generating the intermediate image based on the deformable vector field and a function representing breathing of a patient.

2. The dose calculation method of claim 1, wherein the function representing the breathing of the patient is acquired by measuring breathing characteristics of the patient.

3. The dose calculation method of claim 1, wherein the calculating the dose comprises:
calculating a dose of each of the intermediate image and the diagnostic images; and
recalculating the calculated dose of each of the intermediate image and the diagnostic images to correspond to a reference image by referring to the deformable vector field.

4. The dose calculation method of claim 1, wherein the diagnostic images are 4D computed tomography (CT) images, and the simulation is a deterministic simulation or a stochastic simulation.

5. A dose calculation device comprising:
an intermediate image generator configured to generate an intermediate image between a plurality of diagnostic images that are sequentially acquired; and
a dose calculator configured to calculate a dose through a simulation using the plurality of diagnostic images and the intermediate image, and
wherein the intermediate image generator comprises a deformable vector field acquisitor acquiring a deformable vector field indicating a moving direction of voxels between the diagnostic images, and generated the intermediate image based on the deformable vector field.

6. The dose calculation device of claim 5, further comprising:
a storage configured to store a function representing breathing of a patient, wherein
the intermediate image generator generates the intermediate image based on the function and the deformable vector field.

7. The dose calculation device of claim 6, wherein
the function representing the breathing of the patient is acquired by measuring breathing characteristics of a patient.

8. The dose calculation device of claim 5, wherein
the dose calculator calculates a dose of each of the intermediate image and the diagnostic images, and recalculates the calculated dose of each of the intermediate image and the diagnostic images to correspond to a reference image by referring to the deformable vector field.

9. A non-transitory computer-readable storage medium, the non-transitory computer-readable storage medium having saved thereon at least one program comprising commands for executing a dose calculation method by a processor of a computer when the program is executed by the computer, the dose calculation method comprises:
generating an intermediate image between a plurality of diagnostic images that are sequentially acquired; and
calculating a dose through a simulation using the plurality of diagnostic images and the intermediate image,
wherein the generating the intermediate image comprises:
acquiring a deformable vector field indicating a moving direction of voxels between the diagnostic images; and
generating the intermediate image based on the deformable vector field and a function representing breathing of a patient.

10. The non-transitory computer-readable storage medium of claim 9,
the function representing the breathing of the patient is acquired by measuring breathing characteristics of a patient.

11. The non-transitory computer-readable storage medium of claim 9, wherein the calculating the dose comprises:
calculating a dose of each of the intermediate image and the diagnostic images; and
recalculating the calculated dose of each of the intermediate image and the diagnostic images to correspond to a reference image by referring to the deformable vector field.

12. The non-transitory computer-readable storage medium of claim 9, wherein
the diagnostic images are 4D computed tomography (CT) images, and
the simulation is a deterministic simulation or a stochastic simulation.

* * * * *